United States Patent [19]

Fritzsche

[11] 4,059,983
[45] Nov. 29, 1977

[54] PROCESS FOR THE DETERMINATION OF THE VISCO-ELASTIC CHARACTERISTICS OF POLYMERS AND ARRANGEMENT TO CARRY OUT THE PROCESS

[75] Inventor: Christoph Fritzsche, Villars-sur-Glane, Switzerland

[73] Assignee: Lonza, Ltd., Gampel, Switzerland

[21] Appl. No.: 719,708

[22] Filed: Sept. 2, 1976

[30] Foreign Application Priority Data

Sept. 2, 1975 Switzerland .............................. 11351

[51] Int. Cl.$^2$ .............................................. G01N 3/54
[52] U.S. Cl. ........................................ 73/15.6; 73/101
[58] Field of Search ...................... 73/9, 15.4, 15.6, 78, 73/101, 159

[56] References Cited

U.S. PATENT DOCUMENTS

| | | | |
|---|---|---|---|
| 2,070,731 | 2/1937 | Henning | 73/101 |
| 2,296,657 | 9/1942 | Wallace | 73/9 |
| 3,643,490 | 2/1972 | Hertel | 73/9 |
| 3,718,028 | 2/1973 | Moser | 73/15.4 |

*Primary Examiner*—Herbert Goldstein
*Attorney, Agent, or Firm*—Virgil H. Marsh

[57] ABSTRACT

A process for the determination of the visco-elastic characteristics of polymers which includes stimulating a rolling pendulum which is supported on a flat horizontal surface of a polymer sample, to free, attenuated rolling oscillations at different temperatures of the polymeric sample and measuring the attenuation and/or material frequency of the rolling oscillations in dependence on the temperature of the polymeric sample.

An apparatus for carrying out such process which includes a table for the accommodation of the sample, which has a flat surface, means for heating or cooling of the table top to certain temperatures, means for adjustment of the table, whereby the flat surface of the polymeric sample is positioned in the a horizontal position, a rolling pendulum that is supported by the surface of the polymeric sample, and means for the reading of the oscillations of the rolling pendulum.

18 Claims, 6 Drawing Figures

U.S. Patent  Nov. 29, 1977  4,059,983
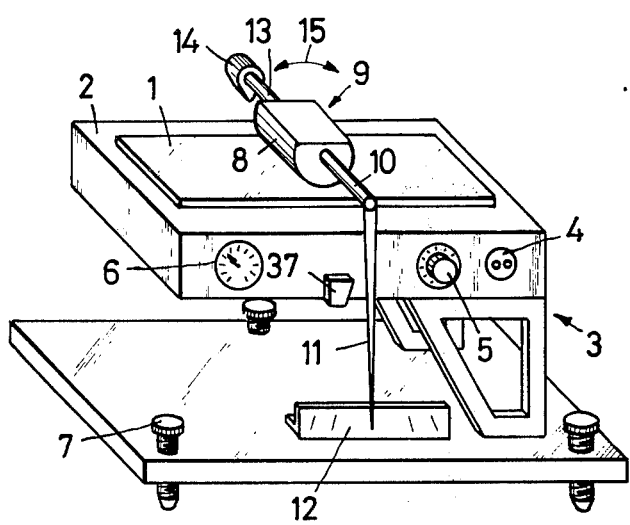
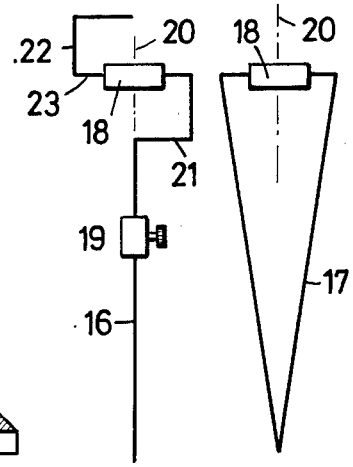
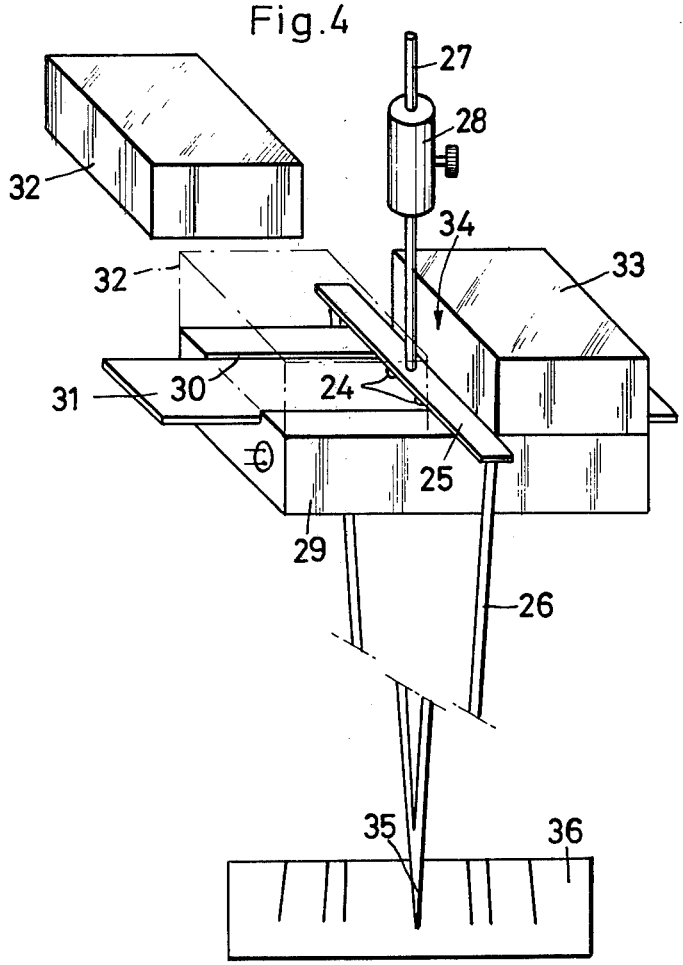

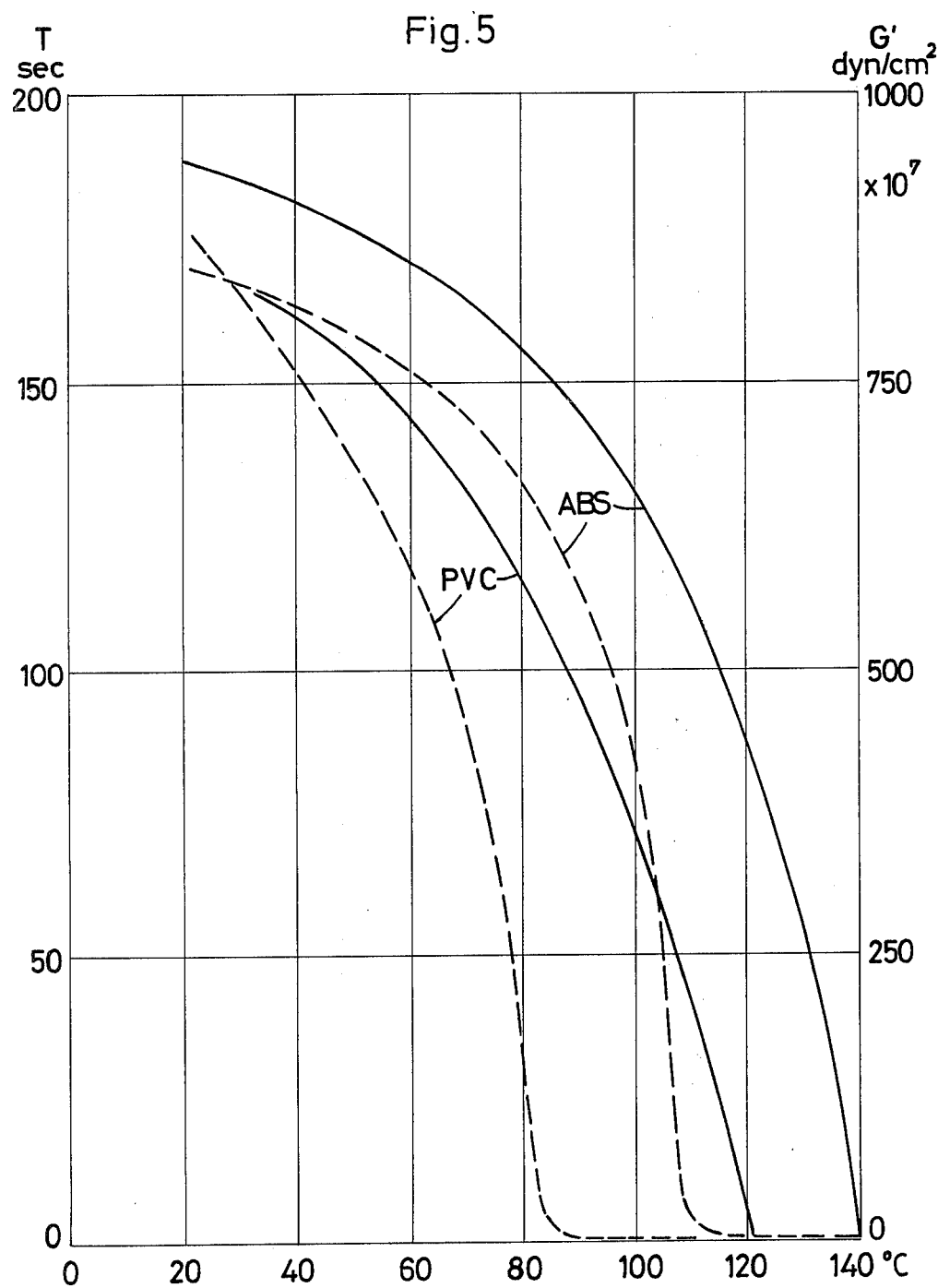

PROCESS FOR THE DETERMINATION OF THE VISCO-ELASTIC CHARACTERISTICS OF POLYMERS AND ARRANGEMENT TO CARRY OUT THE PROCESS

BACKGROUND OF THIS INVENTION

1. Field of this Invention

This invention relates to a process for the determination of the vasco-elastic characteristics of polymers and an arrangement for conducting the process.

2. Prior Art

The visco-elastic characteristics of polymers have been determined by means of a torsional oscillation apparatus. In that case a test strip of certain dimensions from the pertinent polymer is held first at one end and, at the other end, an oscillation body is attached; the pendulum formed thereby is stimulated as a result thereby in a heatable chamber to torsional oscillations, and the frequency and attenuation of the oscillations is measured. The known process is indeed simple in principle and it makes possible a precise determination of the physically defined elasticity and rigidity moduli and of the attenuation. But execution of such process is cumbersome and time consuming and correspondingly expensive.

For example, it is cumbersome to get the test strip, as required, exactly symmetrical with regard to the torsion pendulum axis in the apparatus and to insert it in its clumped state into its heatable chamber. The process is time consuming because the test strip lies unfettered in the chamber on its periphery, and thus can be heated or cooled only by radiation and convection.

The constant measuring frequency over the entire temperature range, which is to be strived for from the physical point of view, cannot be achieved, or can only be achieved only at additional cost, with known torsional oscillation apparatus.

The known process also has the basic disadvantage created by the principle of measurement in that mesurements can only be made in the range of temperatures at which the test strip can be used as a torsion of a torsion pendulum. Above a certain softening temperature, no measurements can be made according to this principle.

The reasons why the known torsional oscillation apparatuses are expensive and correspondingly costly are that various problems occur during execution of the known process.

The precise clamping down of the test strip in the correct position with respect to the vibrating body requires a special clamping apparatus. It is difficult to stimulate the pendulum to carry out a purely rotating oscillation, i.e., to avoid translatory oscillation components, which would lead to errors in measurement. The oscillation amplitudes of only a few angular degrees, which are small in the linear elasticity range for the purpose of measurement, can be measured only by means of Poggendox's reading by reflection or by means of a precisely operating electromechanical converter. While passing through the temperature range, the test strip is gradually twisted, whereby the zero point of the oscillation migrates by a certain amount which in comparison to the amplitude is not negligible under any circumstances.

The test strip therefore must be connected to the oscillating body by a connecting element, rotatable without friction with respect to the heatable chamber, whereby its guidance through the chamber wall must not lead to a significant heat exchange between the space within and the space without the chamber. In order to avoid a longitudinal tension which could distort the measuring results, said strip must be released of the weight of the oscillating body.

The structural solution of these problems led the art to expensive and correspondingly costly torsional oscillation arrangements.

For these reasons, the visco-elastic characteristics of polymers could be determined hitherto only in larger research laboratories. There was no simple, little-time consuming process which could be carried out with a reasonably priced apparatus which was available to the practitioner for these purposes.

BROAD DESCRIPTION OF THIS INVENTION

An object of this invention is to provide a process for the determination of the visco-elastic characteristics of polymers. Another object of this invention is to provide apparatus for achieving the above process. Other objects and advantages of this invention are set out herein or are obvious herefrom to one ordinarily skilled in the art.

The objects and advantages of this invention are achieved by the objects and advantages of this invention.

Therefore this invention is based on the object of determining the visco-elastic characteristics of polymers in a simple manner that consumes little time, and which can be carried out using simple apparatus.

The object is solved according to this invention through the fact that a rolling pendulum on a flat, horizontal surface of a polymer sample is induced to carry out free, attenuated rolling oscillations at different temperatures of the sample and that the attenuation for natural frequency of the rolling oscillations is measured in dependence on the temperature of the sample.

A rolling pendulum, as known, includes a cylindrical body, the center of gravity of which lies outside the cylinder axis because of an unequal and unsymmetrical distribution of the mass. Such a rolling pendulum, after deflection from its rest position and under the influence of gravity, carries out a rolling oscillation around a movable axis on a horizontal support.

Naturally the cylindrical body need not be a solid cylinder; it is sufficient if it has a cylindrical surface. It can also be replaced by a sphere or part of a sphere — in such case, the pendulum has two degrees of freedom. With one cylindrical or with two spherical surfaces, the pendulum has only one degree of freedom.

Whenever the roller pendulum oscillates, the pendulum pressing by means its weight on the surface of the test body, carries out a periodically reciprocating rolling movement (rolling oscillation) on the surface of the test body, whereby a periodically changing pressure is exerted, because the pressure loaded spot reciprocates periodically. The periodically changing, corresponding deformation is partly plastic and partly plastic with the transition shapes, that can be observed in polymers, as well as entropy-elastic and visco-elastic. The process does not make possible, to be sure, precise measurements of the physically defined characteristics of the polymer, but under certain assumptions there are relationships between the attenuation of the oscillation of the pendulum and the torsional storage module. Especially the attenuation of pendulum oscillation is a function of the temperature which results in a characterization of the visco-elastic characteristics of the polymer sufficient for many purposes in practice, preferably for purposes of comparison.

At the same time the process of this invention, a compared to known processes, to be carried out with a torsional oscillation device, has the following advantages (among others).

The test body, the dimensions of which are not significance, does not need to be clamped — it is sufficient to place it onto a heatable and/or coolable support. A relief (balancing) of the pendulum is omitted because the pendulum must exert a pressure on the surface of the test body, so that the latter is deformed periodically. The pendulum, whenever it is made with one cylindrical or two spherical rolling surfaces, has only one degree of freedom, so no troublesome oscillation components can occur. Since the pendulum oscillates in a vertical plane, it can be equipped with a long pointer indicating even small deflections that are easily readable without there being any need for large horizontal dimensions of the apparatus. Since only the surface of the test body must be free, the test body can be placed on a heatable or coolable support. The test body quickly assumes the temperature of the support by heat conduction in any case much more quickly than by heat radiation and convection as in the case of the torsional pendulum. Finally, measurement is also possible at temperatures at which the test body is so soft that it would no longer be usable as the torsional body of a torsional pendulum.

Another essential advantage of the process of this invention is its feasibility of use with a very simple and correspondingly not very expensive, as well as easily manageable, apparatus.

The apparatus of this invention has a table for the accommodation of the test body, means (apparatus) for heating or cooling the table top to certain temperatures, means (apparatus) for adjusting the table, the surface of the test body is positioned in the horizontal position, a rolling pendulum supported by the surface of the test body and means (apparatus) for reading the oscillations of the rolling pendulum.

DETAILED DESCRIPTION OF THIS INVENTION

Preferred embodiments of this invention are described below in more detail with the aid of the attached drawings.

In the drawings:

FIG. 1 is perspective front view of an apparatus of this invention for the determination of the visco-elastic characteristics of polymers;

FIG. 2 is a side view of one type of rolling pendulum;

FIG. 3 is a side view of another type of rolling pendulum;

FIG. 4 is a perspective front view of another apparatus of this invention for the determination of the visco-elastic characteristics of polymers, with a rolling pendulum similar to the one shown in FIG. 3, which is shown partly broken away in order to abridge the presentation;

FIG. 5 is a graph of measurement results which were obtained using the apparatus of FIG. 4, compared to results of torsional oscillation experiments.

Figure 6:
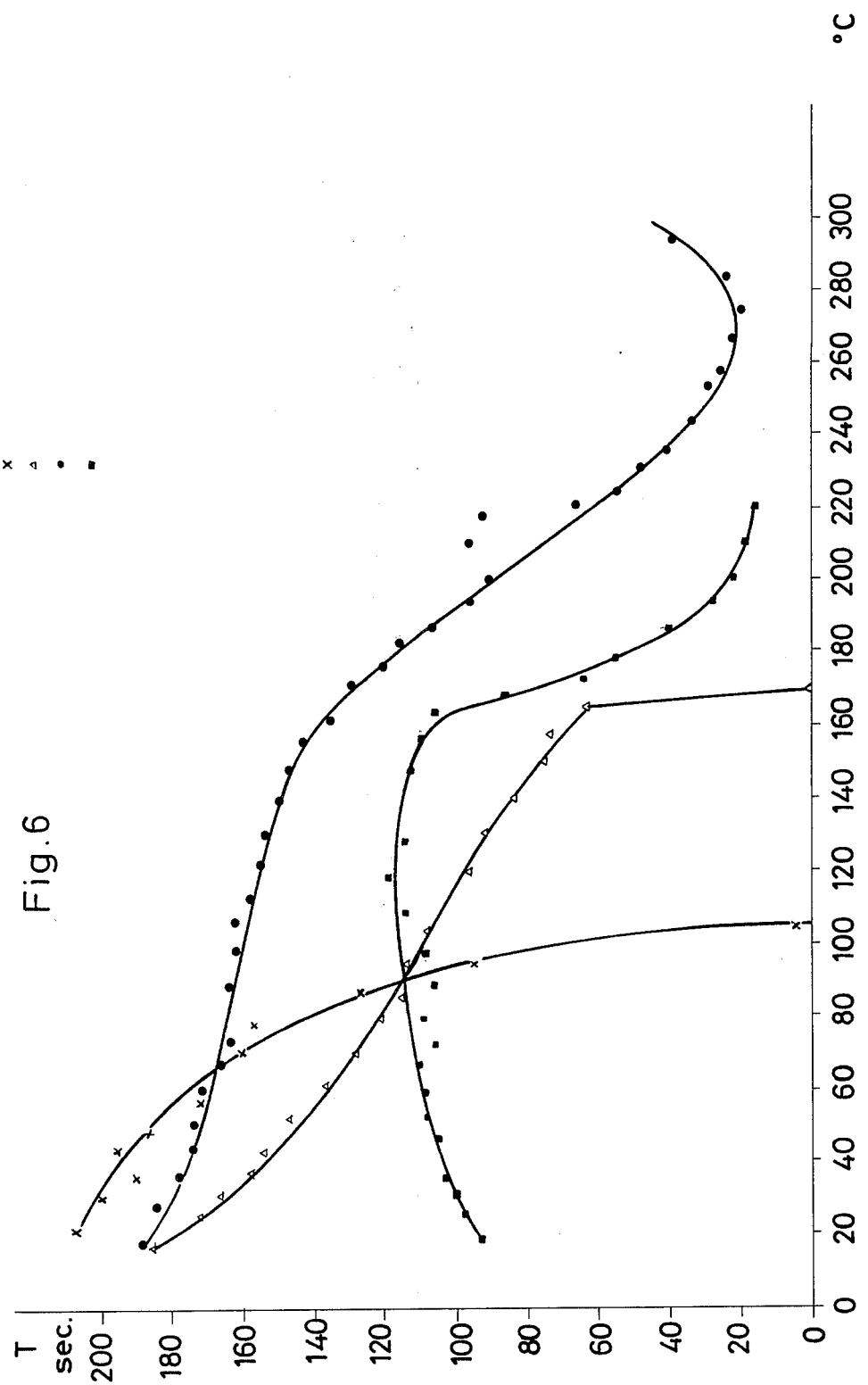
FIG. 6 is a graph of measurement results for different polymers, which were obtained using the apparatus of FIG. 4.

According to FIG. 1, a flat, plane sample of polymer lies on top 2 of table 3. The surface of top 2 is heatable and/or coolable to different temperatures by means of an apparatus inserted into the table top. Of such apparatus, electric connection 4, knob 5 for regulating the temperature and thermometer 6 are shown. Table 3 can be adjusted by means of three adjusting screws 7 such that the surface of its top 2, or of polymeric sample 1, is horizontal. Rolling body 8 of rolling pendulum 9 is placed on the surface of sample 1. Rolling body 8 has the shape of a cylinder segment — it is mounted on a shaft. One end 10 of the shaft projects in FIG. 1 beyond the front edge of table 3 and is equipped with pointer 11. Scale 12, firmly connected to table 3, is assigned (correlated with) pointer 11, from which the deflections of rolling pendulum 9 can be read. The other end 13 of the shaft carries counterweight 14. Counterweight 14, and possibly the other end 13 of the shaft, can be omitted whenever the mass of pointer 11, and possibly end 10 of the shaft, are negligibly small compared to the body of rolling body 8.

Whenever rolling body 8 is swung (swivelled) out of the rest position (shown in one of the two directions of double arrow 15) and is then released, it executes an attenuated rolling oscillation on sample 1. At the same time the zone in which rolling body 8 touches sample 1 reciprocates periodically.

During the contact, sample 1 is compressed by the weight of rolling pendulum 9 and is loaded in shear on the longitudinal sides of this zone. The corresponding deformation is partly elastic, partly plastic, depending on the temperature and the visco-elastic characteristics of the polymer, and partly a delayed deformation takes place and partly a delayed re-deformation. These processes influence the attenuation of the oscillation of rolling pendulum 9, the oscillation process of which can be read from scale 12. In FIG. 1, the center of gravity of rolling pendulum 9, lies within rolling body 8 (whenever the mass of pointer 11 can be ignored as negligible). The center of gravity of rolling pendulum 9 can, however, also lie deeper outside of rolling body 8. For this purpose the rolling pendulum may have pendulum rod 16 or pendulum frame 17, as shown in FIG. 2 or FIG. 3, respectively, whereby the rolling body is 18 and pendulum weight 19 has been provided additionally in FIG. 2. This increases the contact pressure of the pendulum on the surface of the sample and it is shiftable and stoppable on pendulum rod 16 for the purpose of changing the pendulum frequency. In order that the contact pressure, exerted by the rolling body (8:18) of such a rolling pendulum on the sample be distributed uniformly over the contact surface, the center of gravity of the pendulum will have to lie in, for example, the plane designated by 20 in FIG. 2 and FIG. 3, which (plane) directs the rolling body 8 or 18 perpendicularly in relation to its axis.

Whenever the rolling body does not constitute the only part of the pendulum, then this can be achieved most simply with a symmetrical, for example, isosceles triangular pendulum frame 17, shown in FIG. 3, or by right-angle bends 21 and 22 of pendulum rod 16 and of end 23 of the shaft, shown in FIG. 2, whereby right angle bend 21 reaches around the table top and right-angle bend 22 causes a distribution of the mass which is symmetrical in relation to plane 20. Pendulum frame 17 embraces the table top, as becomes clear from FIG. 4.

In the case of the apparatus shown in FIG. 4 (only in its essential parts) the rolling body consists of two small balls which are attached to the underside of traverse 25 of pendulum frame 26, which has the shape of an isosceles triangle.

Balls 24 have equal distance from the middle of traverse 25. On the middle of traverse 25, rod 27 (with mass 28 projecting upwards) has been attached, which is shiftable in order to change the pendulum frequency. Table top 29, equipped with a heating and cooling element (which is not shown), has flat indentation 30 for the reception of polymer sample 31 and bipartite, removable covering 32-33 for the reduction of the heat transfer between the surface of sample 31 and the environment. Between the two parts 32 and 33 of the covering, small space 34 for traverse 25 has been kept free. Lower, pointed end 35 of pendulum frame 26 constitutes a pointer for scale 36.

In case of the rolling pendulum, described in connection with FIGS. 1 to 4, at least the rolling surface of rolling body 8 or 18, or of balls 24, is made preferably of material with poor heat conductivity, so that the pendulum will practically not influence the temperature of its supporting point on sample 1 or 31. For example, rolling body 8 or 18, or balls 24, can consist of glass.

In another embodiment, rolling body 8 or 18, or balls, 24, consists of a heat conducting material. At the same time, rolling body 8 or 18, or each of balls 24, is connected with the shaft (10, 13) or with pendulum rod 16 (the pendulum frame 17) or traverse 25 by an intermediate element (not shown) made of heat insulating material, or else the shaft (10, 13) or pendulum rod 16 (the pendulum frame 17) or traverse 25 consists, at least in the area of their connection with rolling body 8 or 18, or balls 24, of a heat insulating material.

In order to facilitate the stimulation of oscillations with a certain starting amplitude, a stop for the pendulum, disposed in correspondence with this amplitude, or its pointer, in this case to be made sufficiently firmly, can be provided for example on the table top or on the scale, for example, stop 37 in FIG. 1.

In order to determine the visco-elastic characteristics of a polymer, a flat plane sample of that polymer is placed on the table surface of an apparatus as described herein. If need be, the table top is adjusted in order to put the surface of the sample into a horizontal position. The pendulum is supported with its rolling body on the surface of the sample in such a way that its roller axis runs at right angles to the scale and the pointer (in the rest position of the pendulum) points to zero point on the scale. In case of a certain temperature, the pendulum is deflected by a certain starting amplitude and is then released, whereupon it carries out free, attenuated oscillations. As a relative measure of the attenuation, the time inversely proportional to the attenuation can be measured as, a relative mesure of said attenuation, after the lapse of which the oscillation amplitude has dropped to a certain amount. This amount can be marked on the scale. After execution of a measurement, the pendulum is lifted off, the sample is shifted somewhat and the pendulum is put on again, so that every measurement takes place at a point not yet claimed. In this way the attenuation of the pendulum is measured as a function of the temperature.

The temperature dependence of the attenuation can be measured with different parameters, for example, pendulum frequency, contact pressure, radius of the rolling body. Such measurements can also result in clues for delayed elastic and plastic behavior.

The curves of FIG. 5 in solid lines, show the temperature dependence of the attenuation of the oscillations of the pendulum of an arrangement as in FIG. 4 for two thermoplastics, i.e., hard PVC and ABS copolymer Teluran (ABS is the abbreviation for "arylonitrile-butadiene-styrene"), whereby the balls had a diameter of 5 mm, the pendulum weighed 200 gm. and the oscillation time was 1.4 seconds (DIN 53, 157 for evaluation of the hardness of coatings). The decay time, T, inversely proportional to the attenuation, served as a measure of the attenuation, after the lapse of which the amplitude of the pendulum, first deflected to 6°, amounted to 3°. The curves in broken lines in FIG. 5 show the temperature dependence of the torsion-storage module G (determined from the torsional oscillation experiments). This presentation shows that the two thermoplastics cannot only be compared with one another on the basis of expensive apartments using a complicated torsional oscillation arrangement but also by using the simple process of this invention with the simple apparatus of this invention. In practice, the comparison obtained by this invention is sufficient in many instances.

The curves of FIG. 6 show the temperature dependence of the decay time T of the oscillations of the pendulum used for the determination of the solid curves of FIG. 5 for four different polymers, namely, polystyrene, polyoxymethylene, epoxy resin and natural rubber, whereby the presentation corresponds to the FIG. 5. Of the polymers tested, the polystyrene is an amorphous thermoplastic, the polyoxymethylene is partly crystalline thermoplastic, the epoxy resin is a duromer and the natural rubber is an elastomer. The course (configuration) of the curves in FIG. 6 is entirely different for the different polymers. Statements concerning the practical applicability of the polymers as well as concessive as their state at different temperatures can be made on the basis of the shape of the curves. For example, the sequence of the polymers in the case of grouping according to their hardness is always different in different temperature ranges. Furthermore different changes of state, conditional on temperature, can be determined on the basis of characteristic changes of the decay times, T, such as, for example, strong increase in softening of the polystyrene at about 100° C., a melting point of polyoxymethylene between 160° and 170° C., a maximum softening of the epoxy resin at about 275° C., and an increase of its elastic features at higher temperatures, etc.

The oscillation time of the rolling pendulum can also be measured as a function of temperature and can be compared with the oscillation time, which is obtained, whenever the pendulum with its rolling body is supported on a smooth, hard surface, for example, a glass plate or a polished metal plate.

As has already been mentioned, it is not possible with the process and the apparatus of this invention to produce physically defined material contants for scientific purposes but it is possible to make, in any case, very useful determinations sufficient as a rule for practical purposes and to make comparisons.

What is claimed is:

1. A process for the determination of the visco-elastic characteristics of a polymer sample having a flat surface, which comprises the steps of:
   a. spatially arranging the polymer sample so that its flat surface is an upper horizontal surface;
   b. placing a rolling pendulum on the flat horizontal sample surface of the polymer sample, the rolling pendulum being supported thereon in a manner which allows the rolling pendulum to freely roll in an oscillating manner;
   c. varying the temperature of the polymeric sample;

d. concurrently with step (c), exciting the rolling pendulum to free, damped rolling oscillations at the varied temperature of the polymeric sample; and e. measuring the frequency and damping of the rolling oscillations of the rolling pendulum in dependence on the temperature of the polymeric sample.

2. A process as claimed in claim 1 wherein the temperature of the polymeric sample is varied stepwise and after each temperature step the rolling pendulum is displaced on the flat horizontal surface of the polymeric sample, thereby supporting and exciting to rolling oscillations the rolling pendulum at each temperature on another spot of the sample surface.

3. A process as claimed in claim 1 which includes the further steps of:

f. varying the weight of the rolling pendulum; and g. measuring the frequency and damping of the rolling oscillations of the rolling pendulum in dependence on the weight of the pendulum and on the temperature of the polymeric sample.

4. A process as claimed in claim 1 which further includes the further step of:

f. varying the natural oscillation of the rolling pendulum; and g. measuring the frequency and damping of the rolling oscillations of the rolling pendulum in dependence on the natural oscillation of the pendulum and on the temperature of the polymeric sample.

5. A process as claimed in claim 1 which includes the further steps of:

f. varying the radius of curvature of the pendulum area that is to be rolled on the surface of the polymeric sample; and g. measuring the frequency and damping of the rolling oscillations of the rolling pendulum in dependence on the radius of curvature of the surface area of the pendulum and on the temperature of the polymeric sample.

6. An apparatus for the determination of the viscoelastic characteristics of a polymeric sample, which comprises:

a. a table for the accommodation of the polymeric sample, which has a flat surface;

b. means for varying the temperature of the table top;

c. means for adjustment of the table, whereby the flat surface of the polymeric sample is positioned in the horizontal position;

d. a rolling pendulum that is supported on the surface of the polymeric sample; and e. means for the reading of the oscillations of the rolling pendulum.

7. An apparatus as claimed in claim 6 wherein the table top is equipped with a covering having the same temperature as the table top, thus preventing heat loss of the polymeric sample which covering extends at least to the outside range or area where the rolling pendulum is supported by the polymeric sample.

8. An apparatus as claimed in claim 7, wherein the covering has a recess through which a connecting element projects freely, said connecting element connecting at least one rolling body of the pendulum with a pendulum rod or frame.

9. An apparatus as claimed in claim 8 wherein at least one rolling body of the pendulum is connected with the pointer by an intermediate member, consisting of heat insulating material and with the connecting member projecting beyond the table on one or both sides.

10. An apparatus as claimed in claim 6 wherein the surface of the rolling pendulum, that is supported by the polymeric sample and to be unrolled on the pendulum during its oscillation, consists of heat insulating material.

11. An apparatus as claimed in claim 6 wherein the rolling pendulum is connected with a pointer to which a scale connected firmly with the table and divided in the angular measure of the rolling oscillation is assigned.

12. An apparatus as claimed in claim 6 wherein the rolling pendulum has a body adjustable radially in relation to the axis of the curvature of its surface to be unrolled on the polymeric sample, for the purpose of the adjustment of its natural oscillation.

13. An apparatus as claimed in claim 6 wherein the distance of the center of the mass of the rolling pendulum from the axis of the curvature, the surface of which is rolled on the sample, is smaller than the radius of the curvature.

14. An apparatus as claimed in claim 6 wherein the distance of the center of the mass of the rolling pendulum from the axis of the curvature, the surface of which is to be unrolled on the sample, is larger than the radius of the curvature.

15. An apparatus as claimed in claim 14 wherein at least one rolling body of the pendulum is firmly connected with a pendulum rod by a connecting element projecting beyond the table on at least one side, thereby the rolling body is disposed homologously on both sides of a plane normal in relation to the rolling axis and containing the center of gravity of the pendulum.

16. An apparatus as claimed in claim 14 wherein at least one rolling body of the pendulum is firmly connected with an element projecting beyond the table on both sides, which element constitutes a part of a pendulum frame surrounding the table, thereby the rolling body is disposed homologously on both sides of a plane normal in relation to the rolling axis and containing the center of gravity of the pendulum frame.

17. An apparatus as claimed in claim 6 wherein a stop for the rolling pendulum which is assigned to a predetermined oscillation amplitude.

18. An apparatus as claimed in claim 6 wherein the surface of the rolling pendulum to be unrolled on the sample has a cylindrical curvature or is formed by two equal spherical partial surfaces.

* * * * *